(12) United States Patent
Moreno

(10) Patent No.: US 9,737,269 B2
(45) Date of Patent: Aug. 22, 2017

(54) HAND-HELD COMMUNICATOR FOR PATIENT USE

(71) Applicant: Manuel V. Moreno, Williamsport, PA (US)

(72) Inventor: Manuel V. Moreno, Williamsport, PA (US)

( * ) Notice: Subject to any disclaimer, the term of this patent is extended or adjusted under 35 U.S.C. 154(b) by 0 days.

(21) Appl. No.: 14/821,162

(22) Filed: Aug. 7, 2015

(65) Prior Publication Data

US 2016/0038080 A1 Feb. 11, 2016

Related U.S. Application Data

(60) Provisional application No. 62/034,477, filed on Aug. 7, 2014.

(51) Int. Cl.
*G08B 5/22* (2006.01)
*A61B 5/00* (2006.01)

(52) U.S. Cl.
CPC .......... *A61B 5/7475* (2013.01); *A61B 5/6897* (2013.01); *A61B 5/7455* (2013.01); *A61B 2560/0487* (2013.01)

(58) Field of Classification Search
CPC ... A61B 5/4824; A61B 5/6897; A61B 5/7475; A61B 5/7445; A61B 5/743; A61B 5/7415; A61B 5/746; A61B 5/7465; A61B 2560/0487; A61B 2560/0214; A61B 5/7455; A61B 2560/0475
See application file for complete search history.

(56) References Cited

U.S. PATENT DOCUMENTS

| | | | |
|---|---|---|---|
| 6,807,965 B1 | 10/2004 | Hickle | |
| 7,565,905 B2 | 7/2009 | Hickle | |
| 7,931,588 B2 | 4/2011 | Sarvazyan et al. | |
| 8,321,006 B1* | 11/2012 | Snyder | G06T 1/00 600/523 |
| 9,171,131 B2* | 10/2015 | Meyer | G06F 19/363 |
| 2003/0236487 A1* | 12/2003 | Knowlton | A61B 18/1402 604/20 |
| 2004/0078947 A1* | 4/2004 | Sandoval | B25B 27/0071 29/235 |
| 2006/0055544 A1 | 3/2006 | Morguelan | |

(Continued)

*Primary Examiner* — Erin File
(74) *Attorney, Agent, or Firm* — Wendy W. Koba

(57) ABSTRACT

A patient communicator device provides the ability for non-verbal communication between a patient and medical personnel. The device includes a handgrip module that is held by the patient and a display unit for use by the medical personnel, with a communication link coupling the two components together. The handgrip module is formed of a deformable material and encases a power source (i.e., battery) and a pressure-activated switch. The patient squeezes the handgrip module to close the switch and transmit a signal to the display unit. For example, one squeeze may be used to indicate that everything is fine, two squeezes may be used to indicate that the patient is feeling an uncomfortable amount of pain and needs additional medication. These "squeeze" signals take the form of pulses that are passed to the display unit so that the medical personnel remains apprised of the patient's condition, allowing the patient to communicate regarding issues such as anxiety, pain or discomfort.

19 Claims, 2 Drawing Sheets

(56) References Cited

U.S. PATENT DOCUMENTS

| | | | |
|---|---|---|---|
| 2007/0034243 A1* | 2/2007 | Miller | A61H 3/04 |
| | | | 135/67 |
| 2009/0177146 A1 | 7/2009 | Nesbitt et al. | |
| 2011/0066078 A1 | 3/2011 | Sarvazyan et al. | |
| 2011/0166429 A1* | 7/2011 | Sun | A61B 5/0205 |
| | | | 600/301 |
| 2013/0165849 A1* | 6/2013 | Monty | A61M 3/022 |
| | | | 604/30 |
| 2013/0331675 A1* | 12/2013 | Batman | A61B 5/742 |
| | | | 600/365 |
| 2015/0088546 A1* | 3/2015 | Balram | G06F 19/322 |
| | | | 705/3 |

\* cited by examiner

HAND-HELD COMMUNICATOR FOR PATIENT USE

CROSS-REFERENCE TO RELATED APPLICATIONS

This application claims the benefit of U.S. Provisional Application Ser. No. 62/034,477, filed Aug. 7, 2014 and herein incorporated by reference.

TECHNICAL FIELD

The present invention relates to a hand-held communicator for use by a patient and, more particularly, to a hand-held device that uses a squeezing motion by the patient to provide non-verbal communication with medical staff (for example, an anesthesia provider), indicating any type of unpleasant situation including, but not limited to, anxiety, pain or discomfort.

BACKGROUND OF THE INVENTION

It is not always advisable for a patient to be extremely sedated during some procedures, since the sedation may cause sudden involuntary movements. On the other hand, it is never advisable for the patient to be too awake and uncomfortable. One example of this scenario is associated with eye surgeries (such as cataract removal, retina surgery, or the like), which requires the patient to be somewhat sedated, yet remain aware of his/her surroundings. These surgeries require the use of microscopic-based instruments to perform the procedure where any slight movement by the patient (such as trying to indicate pain or another issue) is problematic.

In these cases, the patient is the only one who knows exactly how he/she feels. Thus, if the patient's pain level is being exceeded, he/she should be able to request more sedation or pain control without needing to speak to make this request known. In most situations, however, the patient is unable to talk (for some oral surgery procedures), or should not talk and cause undesirable movement. In situations where the patient's face is covered during a procedure, it is difficult to ascertain the patient's pain level.

Additionally, there are situations where a patient is given general anesthesia for a procedure where a local anesthesia may suffice. For example, if there is a language barrier between the patient and the staff, the staff may opt for the use of a general anesthesia (especially in situations where an interpreter is not permitted in the operating room). Similar problems arise where verbal communication is equally problematic—with a stroke patient, a deaf-mute patient, and the like.

SUMMARY OF THE INVENTION

The problems mentioned above are addressed by the present invention, which relates to a hand-held communicator for use by a patient and, more particularly, to a hand-held device that uses a squeezing motion by the patient to provide non-verbal communication with medical staff (for example, an anesthesia provider), indicating any type of unpleasant situation including, but not limited to, anxiety, pain or discomfort.

In particular, the present invention provides a non-verbal patient communication device for use by medical personnel to create a more comfortable experience for patients. The communicator includes a handgrip module that is held by the patient and a display unit positioned to be viewable by the medical personnel. An electronic cable (or other suitable of communication link) forms a signal path between the handgrip module and the display unit. The handgrip module is formed of a deformable material, with a power source (battery) and pressure-activated switch housed within the module.

In operation, the patient squeezes the handgrip module to assist the medical personnel in understanding the patient's immediate medical condition (e.g., pain level, need to cough or sneeze, etc.) where the squeezing action is sufficient to close the pressure-activated switch and send an electrical pulse to the display unit. For example, one squeeze may be used to indicate that everything is fine, two squeezes may be used to indicate that the patient is feeling an uncomfortable amount of pain and needs additional medication, and a long, continuous squeeze may be used to indicate that the pain is unbearable—or that another "immediate concern" exists (i.e., severe itchiness or a strong need to cough or sneeze) and there is a need to stop the procedure and attend to the immediate and pressing problem. These "squeeze" signals are passed from the handgrip module to the display unit, where the display unit is positioned at a location convenient for the medical personnel to view and respond to patient needs.

An additional feature of the present invention is that the non-verbal patient communication of the present invention may easily be used to express other "medical conditions". For example, if a patient is feeling anxious about an on-going procedure (as opposed to feeling physical pain), a different series of squeezes (or types of squeezes) may be communicated to the medical personnel to allow for the administration of a medication that lessens the anxiety level.

Other and further aspects and embodiments of the present invention will become apparent during the course of the following discussion and by reference to the accompanying drawings.

BRIEF DESCRIPTION OF THE DRAWINGS

Referring now to the drawings, where like numerals represent like parts in several views.

DETAILED DESCRIPTION

Figure 1:
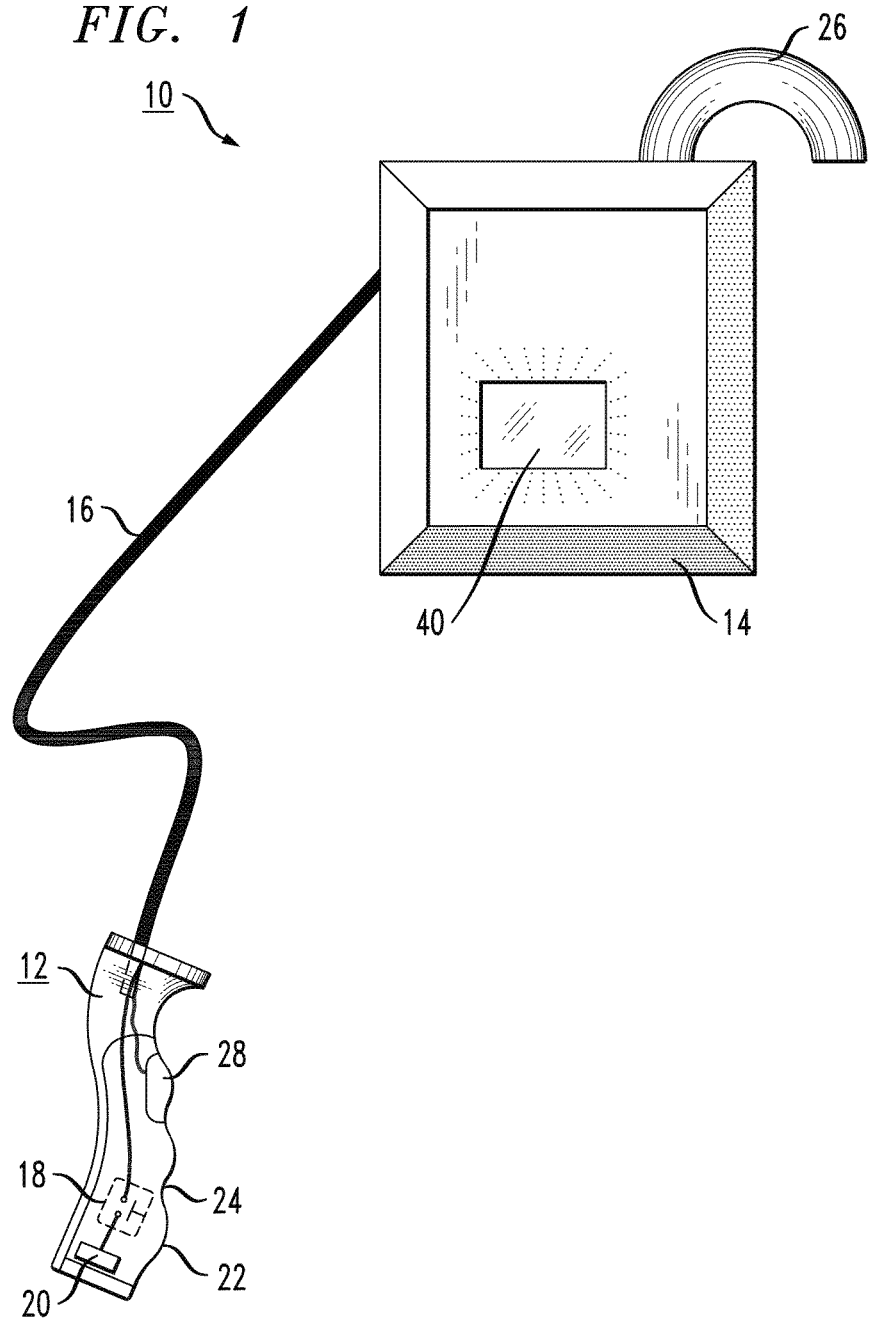
FIG. 1 is a high level diagram of an exemplary hand-held patient communicator formed in accordance with the present invention.

FIG. 1 illustrates an exemplary hand-held patient communicator 10 formed in accordance with the present invention. While reference is made at times to a "pain" indicator (or a "pain" monitor), for the reasons noted above the system of the present invention is useful in situations where any type of "immediate concern" needs to be addressed (e.g., a need to cough, sneeze, anxiety related to the procedure, etc.). Thus, while the term "pain" is used at times in explaining the detailed operation of the present invention, the functionality of the inventive device is of a much broader scope and is generally applicable to providing any type of non-verbal communication between a patient and medical personnel.

Now, with specific reference to FIG. 1, patient communicator 10 includes a handgrip module 12 and a display unit 14, with a communication link 16 disposed between module 12 and unit 14 (it is to be understood that in some situations, a wireless connection be used as the "communication link"). Handgrip module 12, shown in a partial cut-away view in FIG. 1, is shown as including a pressure-activated switch 18 and a power source 20 (such as a battery), both components being encased within a housing 22 formed of a deformable material (such as a plastic). For ease of use, housing 22 may be formed to include indents 24 for finger placement when holding within a patient's grip. In the embodiment of the present invention as shown in FIG. 1, display unit 14 is shown as including a clip attachment 26, which may be used by medical personnel to position display unit 14 in a convenient location.

In accordance with the present invention, when a patient squeezes handgrip module 12, pressure-activated switch 18 will momentarily close, completing an electrical signal path (along communication link 16) between power source 20 and p display unit 14. When the patient stops squeezing handgrip module 12, switch 18 automatically resets in its "off" position and the signal path between power source 20 and display unit 14 is broken. In its broadest sense, by virtue of squeezing handgrip module 12, the patient is able to send a "medical condition" indication signal to display unit 14, allowing the medical personnel to attend to the patient's needs. Various types of medical conditions can be communicated in this manner, including but not limited to, an unbearable pain level, anxiety associated with the procedure, a need to cough, a need to use the bathroom, etc.

Figure 2:
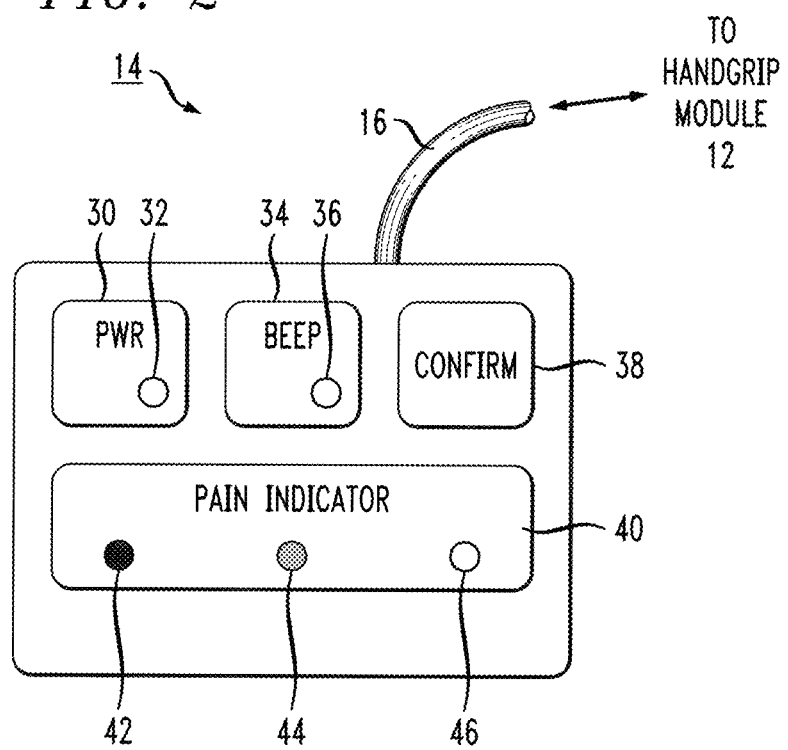
FIG. 2 is a detailed illustration of an exemplary display module, in this case including a pain indicator visual display monitor, formed in accordance with the present invention.

In the particular embodiment as shown in FIGS. 1 and 2, display unit 14 is shown as including a pain panel 40 that creates a pain indication output signal for use by the medical personnel. In a preferred embodiment, indicator panel 40 includes an illumination device (such as an LED) that is lit when handgrip module 12 is squeezed. Alternatively, or in addition to the visible indication, an audible pain level signal may be generated and broadcast by a speaker element included within indicator panel 40. Other types of audible signals that may be created and used (for anxiety problems or other physical issues, for example) will be discussed below in association with FIG. 2.

Thus, by instructing the patient to use a proper number of squeezes to indicate pain level (for example), pressure-activated switch 18 is used to transmit the proper number of pulses to display unit 14 (and, perhaps, causing an LED included within pain indicator display panel 40 to blink on and off). As a result, the patient is able to communicate any issues regarding his/her medical condition to medical personnel without needing to speak. Indeed, it has been found that some patients are hesitant to mention when they have pain, or are unable to express themselves (e.g., stroke victim, language barrier, etc.) so the patient communicator device of the present invention may be useful in a variety of situations other than the few examples mentioned above.

FIG. 2 is a front view of an exemplary display unit 14 that may be used as part of patient communicator 10 formed in accordance with the present invention. In this particular embodiment, display unit 14 is shown as including a power switch 30. This is for use by the medical personnel, and is pressed to turn unit 14 "on". Display unit 14 may itself be battery operated and/or able to operate off of AC voltage from a standard electrical outlet.

In the specific embodiment shown in FIG. 2, power switch 30 includes an LED indicator 32 that will illuminate when power switch 30 is turned "on". Display unit 14 may then be turned "off" by again pressing and releasing power switch 30. When properly turned "off" LED indicator 32 will also turn "off".

Display unit 14 as shown in FIG. 2 also includes a sound switch 34. The inclusion of an audio communication feature is considered to be useful, but is not necessary in all embodiments of the present invention. Upon activation of sound switch 34 (pressing sound switch 34 to turn "on", as confirmed by LED indicator 36), audio messages are also provided as part of the functioning of the inventive pain monitor. For example, when the patient indicates that he/she is comfortable (e.g., by squeezing handgrip module 12 a single time), display unit 14 may play a recorded message saying "I'm OK" (or any similar type of expression of acceptable level of comfort). Other suitable expressions associated with different pain levels and other conditions are also recorded and stored as files within a microprocessor portion (not shown) of display unit 14. In situations where the staff needs silence during a procedure, sound switch 34 may be turned "off" and the sounds muted. For example, a series of three squeezes may be used by the patient to indicate the need to cough, and the audio message may simply state "need to cough". Two "long" squeezes may be used to indicate that the patient is anxious and needs a specific medication to address that concern.

In particular configurations where audio messages associated with both the patient and the medical personnel are stored in unit 14, sound switch 34 may be formed to include separate settings to allow for various possibilities; for example, "muting" only the patient responses, "muting" only the provider responses, or "muting both". Indeed, as mentioned above, there may be some situations where the surgeon and others involved with a procedure would be distracted by audio messages. However, inasmuch as incorporating the audio responses is considered to be beneficial to members of the medical staff, the "default" condition for sound switch 34 is to be "off", requiring medical personnel to make the decision to turn "on" the audio portion of display unit 14.

A preferred embodiment of display unit 14 further includes a "confirm" switch 38. When depressed, confirm switch 38 is used to send a signal from display unit 14 back to handgrip module 12 (perhaps along a separate signal line included within communication link 16). With reference to FIG. 1, the signal generated by confirm switch 38 is shown as being applied as an activation input to a vibration component 28 located within handgrip module 12. Thus, when the medical personnel activates confirm switch 38, the patient is able to feel the vibration and knows that the personnel has responded to his/her needs. While in some cases the medical personnel may be able to communicate verbally with the patient, there are many situations where verbal communication is not possible—particularly in situations where the patient has some hearing loss or there is a language barrier.

FIG. 2 also illustrates a specific embodiment of pain indicator panel 40, formed as part of display module 14. In this specific embodiment, a set of three pain levels associated with a set of three LEDs 42, 44 and 46 is included in indicator panel 40. In preferred configurations of this embodiment, LED 42 is "green" and is associated with the situation where the patient is comfortable and feeling relatively little or no pain. Thus, when the medical personnel inquires about the patient's pain level, and the patient squeezes handgrip module 14 a single time (for example), the associated single pulse output from pressure-activated switch 18 will pass through communication link 16 to unit 14 and be coupled to a receiving device (not shown) within unit 14 that translates a single received pulse to a command to activate LED 42. At the same time, if sound switch 34 is "on", an audio response such as "I'm okay" may be announced.

In a similar fashion, if a patient is feeling some uncomfortable pain at any time during a procedure, he/she may squeeze handgrip module 12 twice (for example), with the two pulses then passing through to unit 14 and activating LED 44. Preferably, LED 44 is "yellow", providing a cautionary message to the medical personnel that the patient is starting to feel some pain and needs some medication. If the situation arises where the patient's pain threshold has been exceeded, the patient is instructed to squeeze handgrip 12 for a relatively long period of time (which may be a natural reaction, regardless of instruction). In response to this "long", continuous signal from handgrip module 14, LED 46 of unit 14 will be activated (where in a preferred embodiment, a "red" device may be used as LED 46). Again, if sound switch 34 is "on", the "yellow" and "red" conditions may have associated announcements. For example, the audio message associated with yellow LED 44 may be something like "I need more sedation" and the message associated with red LED 46 may be something simple such as "please stop".

While the embodiment illustrated in FIG. 2 utilizes a set of three separate LEDs for indicating different circumstances, another embodiment of the present invention may use a single source of illumination. In this alternative, the indicator light would change color, depending on the number of squeezes from the patient. Other LEDs may be used to indicator other medical conditions that also demand immediate attention (i.e., anxiety, a need to move, cough, etc.).

It is preferable that pain indicator panel 40 be configured such that the illuminated pain indicator LED stays "lit" until confirm switch 38 is pressed by the medical personnel. This type of "feedback" allows the patient to know that the message has been successfully transmitted and the condition is being attended to.

While shown with only three pain levels, it is to be understood that either fewer levels (i.e., indicating only "pain" or "no pain") or more levels may be implemented. And while the specific indicator unit as shown in FIG. 2 utilizes LEDs as the "indicators", various other arrangements may be used, including, for example, a touch pad (such as an iPad or similar device) having a graphical user interface (GUI) that displays both the switches and the pain indicators, and can be manipulated by the medical personnel in a manner similar to the LED-based model of FIG. 2.

Indeed, various other modifications and features may be envisioned for use in or with the inventive hand-held patient communicator, both in terms of the features of the handgrip module and the display unit. All are considered to fall within the scope of the invention, which in its broadest terms describes a device that allows for a patient to non-verbally communicate with medical personnel.

What is claimed is:

1. A hand-held patient communicator, comprising:
   a handgrip module formed of a deformable material and housing a power source, a pressure-activated switch and an output signal path, with the pressure-activated switch coupled between the power source and the output signal path;
   a display module including
      an indicator panel providing a representation of an individual's immediate medical condition, controlled by the activation of the pressure-activated switch; and
      a message confirmation switch, for use by the personnel; and
   a communication link coupled between the handgrip module and the display module, where the application of pressure to the pressure-activated switch indicates a patient's immediate medical concern, the activation of the pressure-activated switch transmitting a medical condition indication signal to the display module to provide a non-verbal communication of the individual's immediate concern to the medical personnel, and wherein upon receipt of the medical condition indication signal, the message confirmation switch is activated by the personnel to transmit a confirmation signal via the communication link to the handgrip module.

2. The hand-held patient communicator of claim 1 wherein the handgrip module is formed of a deformable plastic material.

3. The hand-held patient communicator of claim 1 wherein the handgrip module further comprises a set of indentations on an exterior surface thereof, the set of indentations forming a grip location of the handgrip module.

4. The hand-held patient communicator of claim 1 wherein the power source of the handgrip module comprises a battery.

5. The hand-held patient communicator of claim 1 wherein the patient's immediate medical condition includes an indication of a current level of pain.

6. The hand-held patient communicator of claim 1 wherein the output signal path of the handgrip module comprises an electrical signal path.

7. The hand-held patient communicator of claim 1 wherein the output signal path of the handgrip module comprises a wireless, RF signal.

8. The hand-held patient communicator of claim 1, wherein the handgrip module further comprises a vibration element, responsive to a return signal entering along the output signal path, to provide a confirmation response indication to a patient holding the handgrip module.

9. The hand-held patient communicator of claim 1 wherein the display unit includes a battery-operated power source.

10. The hand-held patient communicator of claim 1 wherein the display unit includes a visual display panel for providing a visual representation of a pain signal received as the medical condition signal from the handgrip module.

11. The hand-held patient communicator as defined in claim 10 wherein the visual display panel includes a plurality of indicator lamps, each lamp associated with a different level of pain.

12. The hand-held patient communicator as defined in claim 11 wherein the plurality of indicator lamps comprises a plurality of LEDs.

13. The hand-held patient communicator as defined in claim 12 wherein each LED of the plurality of LEDs comprises a different color LED, each color associated with a different level of pain.

14. The hand-held patient communicator as defined in claim 1 wherein the display unit includes an audio unit for broadcasting an audio representation of the immediate medical condition signal received from the handgrip module.

15. The hand-held patient communicator as defined in claim 14 wherein the audio unit broadcasts messages from and to a person holding the handgrip module.

16. The hand-held patient communicator as defined in claim 14 wherein the audio unit is configured to controllably mute audio broadcasts from the person, to the person, and both from and to the person.

17. The hand-held patient communicator as defined in claim 14 wherein the display unit includes a memory element for storing a plurality of audio files, each separate audio file associated with a different medical condition signal received from the handgrip module.

18. The hand-held patient communicator as defined in claim 1 wherein the visual illumination of the visual display panel remains "on" until the message confirmation switch is activated.

19. The hand-held patient communicator as defined in claim 1 wherein the handgrip module further comprises a vibration component that is responsive to the confirmation signal received from the display unit.

* * * * *